United States Patent [19]

Le Francier et al.

[11] 4,427,659

[45] Jan. 24, 1984

[54] MURAMYL PEPTIDE SUBSTITUTED ON A PEPTIDE NITROGEN AND MEDICAMENTS CONTAINING THE SAME

[75] Inventors: Pierre Le Francier, Bures sur Yvette, France; Francoise Audibert, Neuilly sur Seine; Jean Choay; Louis Chedid, both of Paris; Edgar Lederer, Sceaux, all of France

[73] Assignee: Agence Nationale de Valorisation de la Recherche (ANVAR), Neuilly sur Seine, France

[21] Appl. No.: 337,503

[22] Filed: Jan. 6, 1982

Related U.S. Application Data

[63] Continuation of Ser. No. 123,054, Feb. 20, 1980, abandoned.

[30] Foreign Application Priority Data

Feb. 20, 1979 [FR] France ................................ 7904316

[51] Int. Cl.$^3$ ..................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,094,971 | 6/1978 | Chedid et al. | 260/112.5 R |
| 4,101,536 | 7/1978 | Yamamura et al. | 424/177 |
| 4,101,649 | 7/1978 | Adam et al. | 260/112.5 R |
| 4,185,089 | 1/1980 | Derrien et al. | 260/112.5 R |

FOREIGN PATENT DOCUMENTS 2655500 6/1977 Fed. Rep. of Germany .
2015534 9/1979 United Kingdom .

OTHER PUBLICATIONS

R. R. Acad. SC. Paris, t.284 (Jan. 31, 1977) 405–408.
Proc. NatAcad. Sci. 73, 1976, 2472–2475.
Biochem. and Biophys. Res. Commun. 66, 1975, 1316–1322.
Biochem. and Biophys. Res. Commun. 72, 1976, 339–346.
Symposium Internatl. les Immunostimulants Bacteriens (Structures Chimiques, Mecanismes d3 Action Applications) Paris, Institut Pasteur Oct. 14, 1974 Resumes' de Communication Abstract.
Biken Journal, vol. 18, 105–111 (1975).

Primary Examiner—Delbert R. Phillips
Attorney, Agent, or Firm—Weiser & Stapler

[57] ABSTRACT

The invention relates to novel compounds of the muramyl-peptide type and to their uses. The muramyl-peptides according to the invention comprise at least two aminoacyl residues in the peptide chain, the second of these aminoacyl residues being D-glutamyl, and they are characterized in that the nitrogen of the first aminoacyl, and forming part of the pepetide linkage connecting the muramyl group to the peptide residue, is substituted by an alkyl group. These compounds are useful notably for the preparation of pharmaceutical compositions, in particular by reason of their regulatory properties on the immune responses of the organism.

18 Claims, No Drawings

MURAMYL PEPTIDE SUBSTITUTED ON A PEPTIDE NITROGEN AND MEDICAMENTS CONTAINING THE SAME

This is a continuation, of application Ser. No. 123,054, filed Feb. 20, 1980, abandoned.

BACKGROUND OF THE INVENTION

1. Field of the Invention

The invention relates to novel compounds endowed with biological and pharmacological properties of great value, and notably among these products, those which show immune mechanism regulating properties.

The invention also relates to the applications of these novel products, to the compositions which are specially suitable for their application and to methods of treating animal or human hosts by administering these novel compounds.

2. Description of the Prior Art

As is known considerable efforts have been consacrated for a long time to research for agents endowed with immune reaction regulating properties. These researches have led first to the preparation of extracts of natural products notably of fragments of peptidoglycans from mycobacteria walls, then to synthetic molecules with relatively small molecules. Series of products with very interesting properties are thus available.

In the course of these researches, at the same time as these novel products novel properties have appeared, and in the same way, novel possibilities of utilization. In consequence, the necessity was felt of finding products responding better to the uses arising from the application of these novel properties, whether it relates to facilitating one or several types of activity to the maximum, whether it is desired to split the various possible activities to have available products with a very specific action, or again whether it is desired to reduce or eliminate certain undesirable side effects.

To arrive at these objectives, one is obliged to modify certain forms of administration, but above all researches have been undertaken to modify the activity of the compounds concerned by varying certain elements of their structure.

In previous work, certain authors have attempted to establish relationships between certain configurations or structural elements and the appearance of given properties, or again between various properties of this type of product. Thus Japanese researchers have observed, in a publication (SHOZO KOTANI AND COLL., Biken Journal, Vol. 19, 9–13, 1976), that there existed an apparent correlation between the immune adjuvant effect of these substances and the pyrogenic effect which can appear in certain experimental conditions, notably for the administration of high doses.

SHOZO KOTANI and coll. have offered the hypothesis that this pyrogenicity could possibly be attributed to the relationship between the compounds concerned and the fragments of peptidoglycans which can be obtained from gram-positive bacteria. Again in this publication, the authors assumed that there could exist a relationship between the mechanisms taking part in the immune responses under the effect of antigen stimulation and those taking part in the regulation of the temperature of the body or of the febrile response. They observe in fact that, among the compounds that they have tested, the most adjuvant are also the most pyrogenic.

The pyrogenic character of these substances can constitute a drawback which is not negligible. If this character is very marked, the administration of the substance can trigger, a dangerous phenomenon of thermal shock in the subject treated. In another connection, even when the pyrogenic character is slight or is only manifested at relatively high doses, it results nonetheless in limitations of use which may be troublesome. The doses used must be controlled rigorously, or again, certain methods of administration, in particular the intravenous route, must be avoided.

For these reasons, it is still important to have available novel substances of this type offering a widened choice of combinations of properties and thus enabling better adaptation of the contemplated use. It is in this sense, that the researches which resulted in the invention, were undertaken.

One improvement aimed at by the researches which led to the present invention was the increase in the activity of the compounds of this type for a particular dose, notably by attempting to reduce the speed of catabolism of the product by the organism of the host to whom it is administered. More particularly, an object of these researches was the synthesis of products more resistant to enzymatic hydrolysis.

Another object of the invention was to enable if necessary the establishment of novel pharmacological properties or combinations of properties, or again their increase to a level not hitherto obtained. With this in view, it was particularly desirable to have available products of which the therapeutic index, that is to say the ratio of the effective doses to the limiting doses for which undesirable phenomena commence to appear is as large as possible.

The desired improvements and modifications have been achieved, at least in part, by the products according to the present invention, notably in that adjuvant products are obtained which do not manifest any pyrogenic effect, which facilitates their use by leaving a wide latitude in the mode of administration (notably by the intravenous route) and in the dose administered without the risk of deleterious side effects.

GENERAL DESCRIPTION OF THE INVENTION

The products according to the invention are of the muramyl-peptide type, the peptide chain including at least two aminoacids, the second aminoacid fixed to the muramyl residue being D-glutamyl.

The nitrogen entering into the peptide linkage joining the muramyl group to the peptide residue is substituted, preferably by an alkyl group, so that the action of proteolytic enzymes at this particular point is prevented.

The alkyl group substituting the nitrogen of the first peptide linkage is preferably a group containing a small number of carbon atoms (1 to 3) and more particularly a methyl group.

Advantageous products according to the invention have the structure corresponding to the general formula

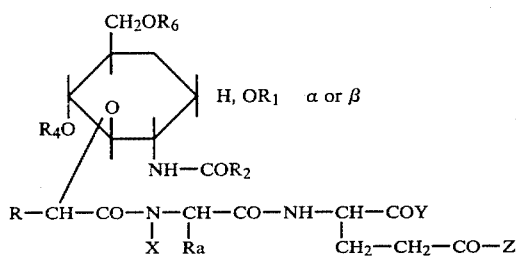

$$R-CH-CO-N-CH-CO-NH-CH-COY \quad (I)$$
$$\phantom{R-CH-CO-N-C}|\phantom{H-CO-NH-C}|$$
$$\phantom{R-CHC}X\phantom{OCO}Ra\phantom{COCONHCH}CH_2-CH_2-CO-Z$$

in which the substituents have the following meanings:

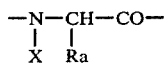

in an aminoacyl residue in which Ra is —$CH_3$ or —$CH_2OH$, X representing an alkylgroup containing 1 to 3 carbon atoms;

Y is either —OH, or an alkoxy radical comprising from 1 to 10 carbon atoms, or —$NH_2$ group, the hydrogens of the amino group being substituted by alkyl residues comprising from 1 to 10 carbon atoms; or again a substituted or unsubstituted amino-acid residue;

Z is —OH, —$NH_2$ or again an alcoxy radical of 1 to 10 carbon atoms;

R is either a hydrogen atom, or an alkyl group comprising from 1 to 4 carbon atoms;

$R_1$ is a hydrogen atom;

$R_2$ is a hydrogen atom or an alkyl, aryl or alkyl-aryl group possibly substituted and including at the most 22 carbon atoms;

$R_4$ is a hydrogen atom or an acyl radical comprising at the most 4 carbon atoms;

$R_6$ is a hydrogen atom, a saturated or unsaturated acyl group, possibly branched, containing from 1 to about 90 carbon atoms and being able in addition to carry functional groups: hydroxyl, carboxyl, amino, cyclopropane, methoxyl.

Preferred compounds of formula (I) are those for which —NX—CHRa—CO— is an al-anyl or seryl residue substituted on the nitrogen and preferably of the natural L series.

Preferably, Y is —OH, —$NH_2$, —$OCH_3$, —$OC_4H_9$, —$OC_{10}H_{21}$, in the compounds of formula (I).

In a preferred form, Z, in the formula (I) represents either —OH, or —$NH_2$, or again —$OCH_3$, —$OC_4H_9$, —$OC_{10}H_{21}$.

In the most usual preferred form, that is to say that for which the structure of muramic acid occurs, R is —$CH_3$. In another preferred form, the R group is a hydrogen; the structure of the lower homologue denoted by the name nor-muramic acid is then found. Finally, in another preferred form, R is —$C_2H_5$; so-called homo-muramic structure corresponds to this form.

The hydroxyl borne by the anomeric carbon in the saccharide portion of the products according to the invention can be in α or β form. This oside residue can also receive different substituents of which the prior art, relating to adjuvant agents of the muramyl peptide type, has given a certain number of examples. In particular the literature described products of which the functional groups of the oside residue are substituted by ester or ether groups for the hydroxyls, and by amide groups for the amino radical at the 2 position.

In the general formula of the products according to the invention, the substituents of the glucopyranoside ring have been denoted by $R_1$, $R_2$, $R_4$ and $R_6$. The various positions do not have the same possibilities of substitution, the 6 position being that for which the greatest latitude is offered.

Preferred compounds are those in which one or several of the substituents $R_1$, $R_4$ and $R_6$, independently of one another or simultaneously, are hydrogen.

Advantageous compounds are also those for which $R_4$ is the acetyl group.

Preferred compounds are also those for which $R_6$ is an acyl radical containing from 1 to 4 carbon atoms, and notably the acetyl radicals (—$COCH_3$), or again those for which $R_6$ is the mycoloyl group (about $C_{80}$ to $C_{90}$) or corynomycoloyl ($C_{32}$).

Preferred $R_2$ substituents are constituted by alkyl groups comprising from 1 to 4 carbon atoms and, it is particularly preferred for $R_2$ to be —$CH_3$.

Among the compounds according to the invention, those are particularly preferred for which $R_1$, $R_4$, $R_6$ are simultaneously a hydrogen atom, and R and $R_2$ are —$CH_3$.

DESCRIPTION OF SPECIFIC EMBODIMENTS

Advantageous compounds are notably:

the N-acetyl-muramyl-N-methyl-L-alanyl-D-isoglutamine, the N-acetyl-muramyl-N-methyl-L-alanyl-D-glutamine-methyl-ester, the N-acetyl-Nor-muramyl-N-methyl-L-alanyl-D-isoglutamine, the N-acetyl-muramyl-N-methyl-L-alanyl-D-glutamine-O-n-butyl ester.

Other preferred compounds are those of formula (I) of which the substituents are shown in the following Tables.

| No. | $R_1$ | $R_2$ | $R_4$ | $R_6$ | R | —NX—CHRa—CO— | Y | Z |
|---|---|---|---|---|---|---|---|---|
| 1 | H | $CH_3$ | H | H | $CH_3$ | N—methyl-L-alanyl ou | —OH | OH |
| 2 | " | " | " | " | " | N—methyl-alanyl | | $NH_2$ |
| 3 | " | " | " | " | " | " | | $OCH_3$ |
| 4 | " | " | " | " | " | " | | $OC_4H_9$ |
| 5 | " | " | " | " | " | " | | $OC_{10}H_{21}$ |
| 6 | " | " | " | " | " | " | —$OCH_3$ | OH |
| 7 | " | " | " | " | " | " | | $NH_2$ |
| 8 | " | " | " | " | " | " | | $OCH_3$ |
| 9 | " | " | " | " | " | " | | $OC_4H_9$ |
| 10 | " | " | " | " | " | " | | $OC_{10}H_{21}$ |
| 11 | " | " | " | " | " | " | $OC_4H_9$ | OH |
| 12 | " | " | " | " | " | " | | $NH_2$ |
| 13 | " | " | " | " | " | " | | $OCH_3$ |
| 14 | " | " | " | " | " | " | | $OC_4H_9$ |
| 15 | " | " | " | " | " | " | | $OC_{10}H_{21}$ |

-continued

| No. | R₁ | R₂ | R₄ | R₆ | R | —NX—CHRa—CO— | Y | Z |
|---|---|---|---|---|---|---|---|---|
| 16 | " | " | " | " | " | " | OC₁₀H₂₁ | OH |
| 17 | " | " | " | " | " | " | | NH₂ |
| 18 | " | " | " | " | " | " | | OCH₃ |
| 19 | " | " | " | " | " | " | | OC₄H₉ |
| 20 | " | " | " | " | " | " | | OC₁₀H₂₁ |
| 21 | " | " | " | " | " | " | NH₂ | OH |
| 22 | " | " | " | " | " | " | | NH₂ |
| 23 | " | " | " | " | " | " | | OCH₃ |
| 24 | " | " | " | " | " | " | | OC₄H₉ |
| 25 | " | " | " | " | " | " | | OC₁₀H₂₁ |
| 26 | " | " | " | " | " | " | NHC₄H₃ | OH |
| 27 | " | " | " | " | " | " | | NH₂ |
| 28 | " | " | " | " | " | " | | OCH₃ |
| 29 | " | " | " | " | " | " | | OC₄H₉ |
| 121 | " | " | " | " | H | " | —OH | OH |
| 122 | " | " | " | " | " | " | " | NH₂ |
| 123 | " | " | " | " | " | " | " | OCH₃ |
| 124 | " | " | " | " | " | " | " | OC₄H₉ |
| 125 | " | " | " | " | " | " | " | OC₁₀H₂₁ |
| 126 | " | " | " | " | " | " | —OCH₃ | OH |
| 127 | " | " | " | " | " | " | " | NH₂ |
| 128 | " | " | " | " | " | " | " | OCH₃ |
| 129 | " | " | " | " | " | " | " | OC₄H₉ |
| 130 | " | " | " | " | " | " | " | OC₁₀H₂₁ |
| 131 | " | " | " | " | " | " | OC₄H₉ | OH |
| 132 | " | " | " | " | " | " | " | NH₂ |
| 133 | " | " | " | " | " | " | " | OCH₃ |
| 134 | " | " | " | " | " | " | " | OC₄H₉ |
| 135 | " | " | " | " | " | " | " | OC₁₀H₂₁ |
| 136 | " | " | " | " | " | " | OC₁₀H₂₁ | OH |
| 137 | " | " | " | " | " | " | " | NH₂ |
| 138 | " | " | " | " | " | " | " | OCH₃ |
| 139 | " | " | " | " | " | " | " | OC₄H₉ |
| 140 | " | " | " | " | " | " | " | OC₁₀H₂₁ |
| 141 | " | " | " | " | " | " | NH₂ | OH |
| 142 | " | " | " | " | " | " | " | NH₂ |
| 143 | " | " | " | " | " | " | " | OCH₃ |
| 144 | " | " | " | " | " | " | " | OC₄H₉ |
| 145 | " | " | " | " | " | " | " | OC₁₀H₂₁ |
| 146 | " | " | " | " | " | " | NHC₄H₃ | OH |
| 147 | " | " | " | " | " | " | " | NH₂ |
| 148 | " | " | " | " | " | " | " | OCH₃ |
| 149 | " | " | " | " | " | " | " | OC₄H₉ |
| 150 | " | " | " | succinyl | CH₃ | " | —OH | OH |
| 151 | " | " | " | " | " | " | " | NH₂ |
| 152 | " | " | " | " | " | " | " | OCH₃ |
| 153 | " | " | " | " | " | " | " | OC₄H₉ |
| 154 | " | " | " | " | " | " | " | OC₁₀H₂₁ |
| 155 | " | " | " | " | " | " | —OCH₃ | OH |
| 156 | " | " | " | " | " | " | " | NH₂ |
| 157 | " | " | " | " | " | " | " | OCH₃ |
| 158 | " | " | " | " | " | " | " | OC₄H₉ |
| 159 | " | " | " | " | " | " | " | OC₁₀H₂₁ |
| 160 | " | " | " | " | " | " | OC₄H₉ | OH |
| 161 | " | " | " | " | " | " | " | NH₂ |
| 162 | " | " | " | " | " | " | " | OCH₃ |
| 163 | " | " | " | " | " | " | " | OC₄H₉ |
| 164 | " | " | " | " | " | " | " | OC₁₀H₂₁ |
| 165 | " | " | " | " | " | " | OC₁₀H₂₁ | OH |
| 166 | " | " | " | " | " | " | | NH₂ |
| 167 | " | " | " | " | " | " | OC₁₀H₂₁ | OCH₃ |
| 168 | " | " | " | " | " | " | " | OC₄H₉ |
| 169 | " | " | " | " | " | " | " | OC₁₀H₂₁ |
| 170 | " | " | " | " | " | " | NH₂ | OH |
| 171 | " | " | " | " | " | " | " | NH₂ |
| 172 | " | " | " | " | " | " | " | OCH₃ |
| 173 | " | " | " | " | " | " | " | OC₄H₉ |
| 174 | " | " | " | " | " | " | " | OC₁₀H₂₁ |
| 175 | " | " | " | " | " | " | NHC₄H₃ | OH |
| 176 | " | " | " | " | " | " | " | NH₂ |
| 177 | " | " | " | " | " | " | " | OCH₃ |
| 178 | " | " | " | " | " | " | " | OC₄H₉ |
| 179 | " | " | " | COCH₃ | " | " | —OH | OH |
| 180 | " | " | " | " | " | " | " | NH₂ |
| 181 | " | " | " | " | " | " | " | OCH₃ |
| 182 | " | " | " | " | " | " | " | OC₄H₉ |
| 183 | " | " | " | " | " | " | " | OC₁₀H₂₁ |
| 184 | " | " | " | " | " | " | —OCH₃ | OH |
| 185 | " | " | " | " | " | " | " | NH₂ |
| 186 | " | " | " | " | " | " | " | OCH₃ |
| 187 | " | " | " | " | " | " | " | OC₄H₉ |

| No. | R$_1$ | R$_2$ | R$_4$ | R$_6$ | R | —NX—CHRa—CO— | Y | Z |
|---|---|---|---|---|---|---|---|---|
| 188 | " | " | " | " | " | " | " | OC$_{10}$H$_{21}$ |
| 189 | " | " | " | " | " | " | OC$_4$H$_9$ | OH |
| 190 | " | " | " | " | " | " | " | NH$_2$ |
| 191 | " | " | " | " | " | " | " | OCH$_3$ |
| 192 | " | " | " | " | " | " | " | OC$_4$H$_9$ |
| 193 | " | " | " | " | " | " | " | OC$_{10}$H$_{21}$ |
| 194 | " | " | " | " | " | " | OC$_{10}$H$_{21}$ | OH |
| 195 | " | " | " | " | " | " | " | NH$_2$ |
| 196 | " | " | " | " | " | " | OC$_{10}$H$_{21}$ | OCH$_3$ |
| 197 | " | " | " | " | " | " | " | OC$_4$H$_9$ |
| 198 | " | " | " | " | " | " | " | OC$_{10}$H$_{21}$ |
| 199 | " | " | " | " | " | " | NH$_2$ | OH |
| 200 | " | " | " | " | " | " | " | NH$_2$ |
| 201 | " | " | " | " | " | " | NH$_2$ | OCH$_3$ |
| 202 | " | " | " | " | " | " | " | OC$_4$H$_9$ |
| 203 | " | " | " | " | " | " | " | OC$_{10}$H$_{21}$ |
| 204 | " | " | " | " | " | " | NHC$_4$H$_3$ | OH |
| 205 | " | " | " | " | " | " | " | NH$_2$ |
| 206 | H | " | " | " | " | " | " | OCH$_3$ |
| 207 | " | " | " | " | " | " | " | OC$_4$H$_9$ |
| 208 | " | —CH$_3$ | " | mycoloyl | " | N—methyl-alanyl. | —OH | OH |
| 209 | " | " | " | " | " | " | " | NH$_2$ |
| 210 | " | " | " | " | " | " | " | OCH$_3$ |
| 211 | " | " | " | " | " | " | " | OC$_4$H$_9$ |
| 212 | " | " | " | " | " | " | " | OC$_{10}$H$_{21}$ |
| 213 | " | " | " | " | " | " | —OCH$_3$ | OH |
| 214 | " | " | " | " | " | " | " | NH$_2$ |
| 215 | " | " | " | " | " | " | " | OCH$_3$ |
| 216 | " | " | " | " | " | " | " | OC$_4$H$_9$ |
| 217 | " | " | " | " | " | " | " | OC$_{10}$H$_{21}$ |
| 218 | " | " | " | " | " | " | OC$_4$H$_9$ | OH |
| 219 | " | " | " | " | " | " | " | NH$_2$ |
| 220 | " | " | " | " | " | " | OC$_4$H$_9$ | OCH$_3$ |
| 221 | " | " | " | " | " | " | " | OC$_4$H$_9$ |
| 222 | " | " | " | " | " | " | " | OC$_{10}$H$_{21}$ |
| 223 | " | " | " | " | " | " | OC$_{10}$H$_{21}$ | OH |
| 224 | " | " | " | " | " | " | " | NH$_2$ |
| 225 | " | " | " | " | " | " | " | OCH$_3$ |
| 226 | " | " | " | " | " | " | " | OC$_4$H$_9$ |
| 227 | " | " | " | " | " | " | " | OC$_{10}$H$_{21}$ |
| 228 | " | " | " | " | " | " | NH$_2$ | OH |
| 229 | " | " | " | " | " | " | " | NH$_2$ |
| 230 | " | " | " | " | " | " | " | OCH$_3$ |
| 231 | " | " | " | " | " | " | " | OC$_4$H$_9$ |
| 232 | " | " | " | " | " | " | " | OC$_{10}$H$_{21}$ |
| 233 | " | " | " | " | " | " | NHC$_4$H$_3$ | OH |
| 234 | " | " | " | " | " | " | " | NH$_2$ |
| 235 | " | " | " | " | " | " | " | OCH$_3$ |
| 236 | " | " | " | " | " | " | " | OC$_4$H$_9$ |
| 237 | " | CH$_2$OH | " | H | " | N—methyl-alanyl | —OH | OH |
| 238 | " | " | " | " | " | " | " | NH$_2$ |
| 239 | " | " | " | " | " | " | " | OCH$_3$ |
| 240 | " | " | " | " | " | " | " | OC$_4$H$_9$ |
| 241 | " | " | " | " | " | " | " | OC$_{10}$H$_{21}$ |
| 242 | " | " | " | " | " | " | —OCH$_3$ | OH |
| 243 | " | " | " | " | " | " | " | NH$_2$ |
| 244 | " | " | " | " | " | " | " | OCH$_3$ |
| 245 | " | " | " | " | " | " | " | OC$_4$H$_9$ |
| 246 | " | " | " | " | " | " | " | OC$_{10}$H$_{21}$ |
| 247 | " | " | " | " | " | " | OC$_4$H$_9$ | OH |
| 248 | " | " | " | " | " | " | " | NH$_2$ |
| 249 | " | " | " | " | " | " | " | OCH$_3$ |
| 250 | " | " | " | " | " | " | " | OC$_4$H$_9$ |
| 251 | " | " | " | " | " | " | " | OC$_{10}$H$_{21}$ |
| 252 | " | " | " | " | " | " | OC$_{10}$H$_{21}$ | OH |
| 253 | " | " | " | " | " | " | " | NH$_2$ |
| 254 | " | " | " | " | " | " | " | OCH$_3$ |
| 255 | " | " | " | " | " | " | " | OC$_4$H$_9$ |
| 256 | " | " | " | " | " | " | " | OC$_{10}$H$_{21}$ |
| 257 | " | " | " | " | " | " | NH$_2$ | OH |
| 258 | " | " | " | " | " | " | " | NH$_2$ |
| 259 | " | " | " | " | " | " | " | OCH$_3$ |
| 260 | " | " | " | " | " | " | " | OC$_4$H$_9$ |
| 261 | " | " | " | " | " | " | " | OC$_{10}$H$_{21}$ |
| 262 | " | " | " | " | " | " | NHC$_4$H$_3$ | OH |
| 263 | " | " | " | " | " | " | " | NH$_2$ |
| 264 | " | " | " | " | " | " | " | OCH$_3$ |
| 265 | " | " | " | " | " | " | " | OC$_4$H$_9$ |

The muramyl-peptide compounds can also, according to the invention be assembled in oligomer form as The products according to the invention are prepared by synthesis or, if necessary, by hemisynthesis. Methods of preparation have been described in the literature for the preparation of compounds of the muramyl-peptide type unsubstituted on the nitrogen of the first peptide linkage. These methods are applicable to the products according to the invention.

Usefully, general methods of preparation for these products are indicated below. Of course, these methods are not the only ones which may be contemplated, and numerous modifications can also be used.

To arrive at a glycopeptide compound, various routes are possible. In all cases, the synthesis includes a series of steps in the course of which the various "fragments" constituting the structure of the group of compounds according to the invention are progressively assembled. The principal differences between the possible routes are situated in the sequence selected for assembling fragments. The reaction methods leading to the fixing of one fragment to the one or more contiguous fragments are on the whole little modified by the order in which this integration is carried out, in so far, of course, as this order depends, on the one hand, on the choice of functional groups which react and which, consequently, must be liberated for the step concerned, and on the other hand, the choice of the group which must be blocked in order not to intervene in the course of this same step.

The preparation of the products according to the invention can be done from corresponding compounds of the muramyl-peptide type. The obtaining of the latter has been described in numerous publications. If necessary, for those whose preparation does not appear expressly in the literature, and notably for the various modifications corresponding to the substitutions of the muramyl group or of similar groups, they may be obtained by following the traditional methods of preparing corresponding derivatives in oligosaccharide chemistry. In the same way, the constitution of the peptide chain linked to the muramic acid is effected according to traditional methods in peptide synthesis.

There are given below succinctly the principal indications relating to the various operations which can be applied to synthetize the products according to the invention, first by considering each step separately, then by indicating some preferred types of sequences.

(a) Formation Of Muramic Acid Or Analogues

To obtain the analogues of N-acetyl-muramic acid of the formula

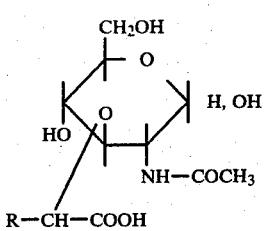

in which R has the previously indicated meaning, it is possible to start from a derivative of N-acetyl-2-deoxy-glucosamine whose hydroxyls in the 1, 4 and 6 position are blocked traditionally. The method of preparing such a derivative, the benzyl-2-acetamido-4, 6-O-benzylidene-2-deoxy-D-glucopyranoside, is described notably by P. H. GROSS and R. W. JEANLOZ (J. Org. Chem. 1967, 32, 2761).

The formation of N-acetyl-muramic acid ($R=CH_3$) or of one of its analogues can be carried out in the manner described in the French Patent application No. 74 22909 or 76 19236 (respectively, for these applications, $R=CH_3$ and $R=H$) taking up the method described by OZAWA and JEANLOZ (J. Org. Chem., 1965, 30, 448).

This formation comprises, for example, the preparation of a sodium salt of the hydroxyl at the 3 position and the subsequent condensation of the sodium derivative with the salt or the ester of a halogenated acid such as chloro-2-propionic or chloroacetic acids to take up again the case of the two previously indicated patent applicatons. The halogenated compound used of the L form may be prepared according to the method described by SINAY and al. (J. Biol. Chem., 1972, 247, 391). By using the appropriate halogenated acids, it is possible to prepare all the derivatives corresponding to the various meanings of R. Thus, to introduce a group R with 4 carbons, the salts or esters of chloro-2-butyric acid may be used.

When a halogenated acid ester is used, in order to be able to proceed with the subsequent peptide condensation, the carboxylic function can be liberated by suitable hydrolysis.

(b) Substitution On The Saccharide Residue

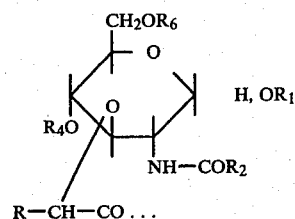

Starting from N-acetyl-muramic derivatives blocked in the 1, 4, 6 positions, as obtained at (a), it is possible to prepare the various analogous compounds in which the acetyl group fixed to the nitrogen in the 2 position is replaced by the substituents whose nature is that given in the general definition, that is to say an alkyl, aryl or alkyl-aryl group possibly substituted and including at the most 22 carbon atoms. For this modification, it is possible to operate in known manner the hydrolysis of the acetyl by a strong base, for example like that described in the publication of P. H. GROSS and JEANLOZ indicated above.

The resulting compound, in which an amino group is in the 2 position of the glucopyranoside ring, can then be again subjected to an acylation treatment, under conventional conditions, with a suitable acylating agent corresponding to the group $R_2$ which is desired to introduce. As acylating agent, acid anhydrous or chlorides may notably be used.

The substituents at the 1, 4 and 6 positions may be carried out by methods which have been described previously and which are conventional in sugar chemistry. When the substituents envisaged are different from one another, as many successive substitution reactions follow as there are distinct substituents. In the course of these reactions, the positions which must not be substituted or those which must consequently be the subject of another substitution are protected temporarily by blocking groups according to the usual methods.

The blocking groups initially present, in the case where one starts, as previously indicated, from benzyl-2-acetamido-4, 6-O-benzylidene-2-deoxy-D-glucopyranoside, are eliminated for example by the action of acetic acid (60% for 1 hour under reflux) and catalytic hydrogenation, as described for example by MERSER and al. (Biochem. Biophys. Res. Commun., 1975, 66, 1316), or by catalytic hydrogenation by the method of LEFRANCIER and al. (Int. J. Peptide Protein Res., 1977, 9, 249).

The methods of substitution are those traditionally used. To obtain the acylated derivatives, procedure is by means of an acylating agent corresponding to the substituent that it is desired to introduce (anhydride, acyl chloride, etc.).

The 1, 4, 6 positions are not equivalent as regards reactivity. The C-6 position is the easiest to substitute, also, when this position alone must be substituted, it is possible to operate without blocking the other positions, with an amount of substitution agent equivalent to that necessary for the substitution of a single position.

A particular example of the method of preparation of the derivatives substituted at the 6position is given in the article of KUSUMOTO and al. (Tetrahedron Letters, 1976, 47, 4237).

The substitutions on the oside residue may be carried out before or after the fixing of the peptide chain or of the fragments of the latter. cl (c) Peptide Chain The synthesis of the N-substituted aminoacids by an alkyl group may be carried out in the manner described for the methyl groups by CHANG S. T. and BENOITON N. L. Can. J. Chem., 1977, 55, 906.

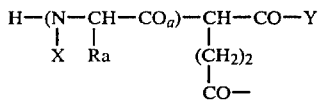

The fixing of a peptide chain to the N-acetylmuramic acid, or to an analogue of the latter such as those which have been indicated above, is obtained by conventional methods in the field of peptide synthesis. Such methods have been amply described in the previous literature and in particular in the previously indicated patent applications.

Generally, the glycopeptide syntheses may be done either by fixing a first aminoacid to the muramyl group, then by fixing to the compound thus obtained the second aminoacid, and so on step by step. It is also possible to prepare separately the entire peptide chain aminoacid by aminoacid and to fix the latter to the muramyl group. It is finally possible to select intermediate methods in which fragments of the chain are prepared, then either to assemble these fragments together to form the complete chain which is then fixed to the muramyl group, or to fix a first fragment to the muramyl group, then a second to the product thus obtained, etc. The choice of the sequence is guided principally by reasons of convenience or of yield.

The Y substitution is advantageously effected on the glutamyl group before the synthesis of the chain.

The peptide syntheses are carried out according to conventional methods. By way of example, it is possible to use the methods of activation of the carboxyls, such as the so-called mixed anhydride method. Advantageously, the peptide synthesis is carried out by means of a compound of the carbodiimide type such as N, N'-dicyclohexylcarbodiimide or equivalent carbodiimides. A review of traditional methods of peptide synthesis is to be found in J. H. JONES, Chemistry and Industry, 723 (1974). It is also possible to refer to the following French Patent applications: 75 29624, 76 06819, 76 06820, 76 06821, 76 21889, 77 02646, and to the article of LEFRANCIER and al. (Int. J. Peptide Protein Res., 1977, 9, 249, 1978, 11, 289).

The formation of the derivatives for which the Y group is either an ester, or an amide, is obtained in known manner. It is possible, in particular, to refer to the above indicated French Patent applications, and notably to application Nos. 76 06820, 76 06821, 76 21889 and 77 02646.

Diagram I represents reaction sequences leading to the production of various glycopeptide derivatives claimed. One starts from a derivative (1) for which the anomeric carbon is protected by a benzyl radical, as described by GROSS and JEANLOZ (J. Org. Chem., 1967, 32, 2759). To obtain the same compound in which $R_1$ is an alkyl or aryl-alkyl group, it is possible to use the method of preparation of the corresponding α or β-glycosides also described in this same article, or any known method for such preparation in oligosaccharide chemistry.

If it is desired to modify the nature of the N-acyl group, the N-acetyl group can be hydrolysed as described again by GROSS and JEANLOZ, to result in derivatives of formula (2). The derivatives (2) can then be selectively N-acylated, notably by the action of carboxylic acid anhydrides to arrive at the derivative of formula (3). The derivatives of formula (4) can be obtained starting from the preceeding ones according to the method described by OZAWA and JEANLOZ (J. Org. Chem. 1965, 30, 448), by means of a L-α-chloroalkanoic acid.

The derivatives of formula (4) are coupled with a peptide derivative of the general formula HN(X)-CH(Ra)-CO-D-Glu-(OZ)-OY hydrochloride, in which formula Y is, for example, an amido-, methylamido-, methoxy- or glycyl-amide group.

These various peptide derivatives are prepared according to the methods described by LEFRANCIER and al. (Int. J. Peptide Protein Res., 1977, 9, 249, and Int. J. Peptide Protein Res., 1978, 11, 289). The coupling methods used to obtain the glycopeptide derivatives of formula (5), as well as the catalytic hydrogenation resulting in the derivatives of formula (6), are also described in the previously mentioned articles. However, both in the synthesis of the dipeptide derivatives and in that of the derivatives of formula (5), any coupling method used in peptide synthesis may be utilised.

Alternatively, the derivatives of formula (5) undergo a selective debenzylidenation such as that described by MERSER and al. (Biochem. Biophys. Res. Commun., 1975, 66, 1316) to give derivatives of formula (8). The selective acylation of the primary hydroxyl at the 6 position of the saccharide residue can then be done directly by the action of a slight excess of carboxylic acid anhydrides or of acyl-imidazole. Derivatives of formula (9) are obtained.

The derivatives of formula (9) may also be synthesised by a totally different sequence (Diagram II, formula 4) similar to that developed by KUSUMOTO and al. (Tetrahedron Letters, 1976, 47, 4237).

In another alternative the derivatives of formula (8) are diacylated on the two hydroxyls at the 4 and 6 positions of the saccharide residue by the action of an excess of carboxylic acid anhydride.

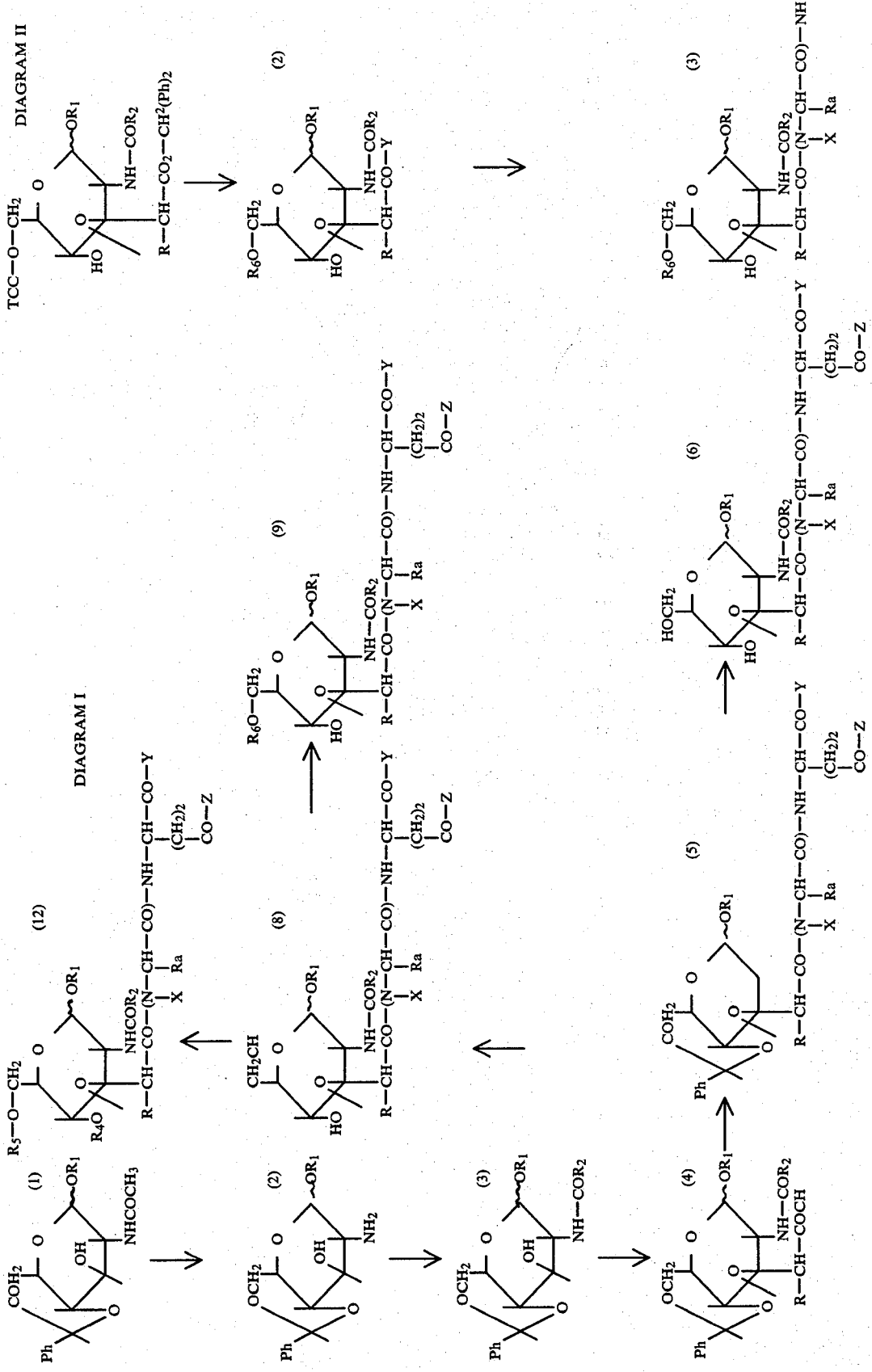

The invention also relates to the methods of utilising compounds corresponding to the preceeding definitions, notably as a reactant or as an active substance in pharmaceutical compositions.

The invention relates to biological reactants, for example, standard immunological adjuvants, which can be constituted by means of the compounds according to the invention, notably in order to study the possible adjuvant properties of substances under investigation, by comparison with such standard adjuvants or, on the other hand, as an agent capable of countering certain effects connected with the administration of immunosuppressive substances.

More particularly, the invention relates to medicaments including, as active principle, at least one of the compounds according to the invention, this medicament being applicable as a regulator of the immune response of the subject to whom it is administered.

These medicaments are notably applicable as a specific immunity adjuvant for the treatment of infectious diseases of bacterial or parasitic or viral origin.

The application of these medicaments is done preventively. This is the case in particular when a reinforcement of the immune response is sought relative to an immunogenic agent. The use of an agent stimulating the immuno system is notably necessary when the immunogenic agent is weak in nature or is derived from a strong agent of which the immunogenic character has been diminished, for example in the course of prior purifications or modifications. The utilisation of a stimulating agent may also be useful if it is desired to utilise very low doses of strong antigens.

The invention relates more particularly also to the application of the compound concerned to the amplification of the immunogenic effect of active principles of vaccines administered to an animal or human host, notably in the case where these vaccinating principles belong to the categories of immunogenic agents recalled above. Consequently, the invention relates also again to pharmaceutical compositions whose active principle is constituted by one at least of the compounds according to the invention, in association with the pharmaceutical vehicle appropriate to the method of administration required or useful having regard to the nature of the vaccinating principle used.

The medicaments according to the invention may be administered to the host—animal or human being—in any suitable manner for the obtaining of the desired effect.

The invention relates naturally also to the various pharmaceutical compositions in which the compounds according to the invention may be incorporated, if necessary in association with other active substances. In particular, the compounds I are advantageously associated with immunogenic agents, whether they are, for example, immunogenic agents which can only be used at very low doses, notably by reason of their poor tolerance, or weak immunogenic agents.

Advantageous pharmaceutical compositions are constituted by injectable solutions or suspensions containing an effective dose of at least one product according to the invention. Preferably, these solutions or suspensions are formed in an isotonic sterilised aqueous phase, preferably saline or glucosed.

The invention relates more particularly to such suspensions or solutions which are adapted to be administered by intradermal, intramuscular or sub-cutaneous injections, or again by scarification.

Other advantageous pharmaceutical compositions are constituted by the liposome forms of the compounds according to the invention. As is known, the liposomes, by reason of the lipid nature (and notably phospholipid nature) of the elements entering into their composition, constitute, for certain cases, a particularly suitable presentation.

The invention also relates to pharmaceutical compositions administrable by other routes, notably by the oral or rectal route, or again in forms intended to come into contact with the mucous membranes, notably the ocular, nasal, pulmonary or vaginal mucous membranes.

Consequently, it relates to pharmaceutical compositions in which one at least of the compounds according to the invention is associated with solid or liquid pharmaceutical acceptable excipients, adapted to the constitution of oral, ocular or nasal forms, or with excipients adapted to the constitution of forms for rectal administration, or again with excipients adapted to vaginal administration, for example gelatinous. It relates finally to compositions intended for the pulmonary route, notably solutions prepared for administration by means of a conventional aerosol device.

The invention consists also of a process seeking to reinforce the immune defences of the host, consisting of administering to it an effective dose of one at least of the products according to the invention, in one of the administrative forms which have been evoked above. By way of example of doses capable of inducing an effect, may be mentioned doses of 10 to 1000 µg per kilogram of body weight, for example 50 µg, when the administration is effected by the parenteral route, or of doses of 200 to 20000 µg per kilogram of body weight, for example 1000 µg, for other methods of administration such as, for example, the oral route.

The invention is described in more detailed manner in the following examples relating to the preparation of products according to the invention, and the various tests relating to the pharmacological properties of these products.

PREPARATION OF PRODUCTS ACCORDING TO THE INVENTION (a)

N-acetyl-muramyl-N-methyl-L-alanyl-D-isoglutamine

The synthesis was done in the manner described by LEFRANCIER and col. (Int. J. of Peptide and Prot. Res., 9, 1977, 249) replacing the L-alanine by N-methyl-L-alanine.

The rotatory power of the product obtained is $[\alpha]_D^{20} = +19.8$ (acetic acid).

| The elementary analysis of the product is for $C_{20}H_{34}N_4O_{11}$ - 0.82 $H_2O$ (M.W. 521.28) | | | |
|---|---|---|---|
| | C | H | N |
| Calculated | 46.07 | 6.89 | 10.75 |
| Found | 46.04 | 6.51 | 10.75 |

(b)

N-acetyl-muramyl-N-methyl-L-alanyl-D-glutamine-methyl-ester

The product, prepared as previously, has the following characteristics:

| Elementary analysis for $C_{21}H_{36}N_4O_{11}$ - 0.2 $CHCl_3$ - 0.3 $CH_3COOH$ | | | |
|---|---|---|---|
|  | C | H | N |
| Calculated | 46.52 | 6.59 | 9.65 |
| Found | 46.55 | 6.70 | 9.96 |

(c)

N-acetyl-Nor-muramyl-N-methyl-L-alanyl-D-isogluta-mine

The product, prepared as previously, has the following characteristics: $[\alpha]_D^{20} = -14.8°$ (glacial acetic acid).

| Elementary analysis for $C_{19}H_{32}N_4O_{11}$, 0.6 $H_2O$ (503.3) | | | |
|---|---|---|---|
|  | C | H | N |
| Calculated | 45.34 | 6.65 | 11.13 |
| Found | 45.34 | 6.5 | 10.95 |

(d)

N-acetyl-muramyl-N-methyl-L-alanyl-D-glutamine-O-n-butyl ester

The product, prepared as previously, has the following characteristics: $[\alpha]_D^{20} = +5.5°$ (glacial acetic acid).

| Elementary analysis for $C_{24}H_{42}O_{11}N_4$, $H_2O$ (580.63) | | | |
|---|---|---|---|
|  | C | H | N |
| Calculated | 49.64 | 7.63 | 9.64 |
| Found | 49.8 | 7.75 | 9.46 |

PHARMACOLOGICAL PROPERTIES (1°) Adjuvant Character In The Aqueous Phase And In Emulsion (a) In the aqueous phase Groups of 8 Swiss mice aged two months receive, by sub-cutaneous injection (SC), 0.5 mg of antigen constituted by bovine serum albumin (BSA) with (0.1 mg) or without the substance under test in an isotonic saline solution. This high dose of antigen, because it is situated at the limit of the paralysing dose with respect to the immune response, results, through this fact, in a weak or nul response to the antigen alone in the controls; it constitutes therefore a severe criterion to establish the activity of an adjuvant substance. Thirty days later, the mice receive, by the same route of administration, a booster containing 0.1 mg of the same antigen.

The anti-body level is determined, before and six days after the booster, by passive hemagglutination using sheep's red blood cells treated with formalin and covered with the antigen under study according to the method described by A. A. HIRATA and M. W. BRANDISS (J. Immunol., 100, 641–648, 1968).

The anty-body titer, represented by the maximum serum dilution agglutinating a given amount of sheep's red blood cells reaches a maximum at the 36th day following the first injection and is estblished in the following manner.

|  | $Log_2$ hemagglutinating titer | |
|---|---|---|
| Products tested | Primary response D 28 | Secondary response D 36 |
| Controls | <1.64 | 3.57 ± 1.78 |
| MDP | 3.64 | 8.34 ± 1.34 |
| MDF-(N—methyl-Ala)* | 4.64 | 9.27 ± 1.19 |
| MDP-(N—methyl-Ala)—$OCH_3$** | | 5.11 |

*N—acetyl-muramyl-N—methyl-L-alanyl-D-isoglutamine
**methyl ester of*

In this table, it is observed that the products according to the invention have a substantial adjuvant effect which may even be greater than that of MDP, notably as regards the primary response. With respect to MDP, however, the principal advantage resides in the very weak pyrogenic character of these products.

(b) In Emulsion

The tests were carried out on batches of 6 Hartley males of 350 g. The administration was done by intradermal injection into the plantar pad of each of the rear paws. Ovalbumin (constituting the antigen) in the proportion of 1 mg is prepared in 0.1 ml of an emulsion of saline isotonic solution, in an oily phase constituted by the Freund incomplete adjuvant (FIA). The compound according to the invention was administered in the emulsion containing the FIA at the doses indicated in the Table of results.

Eighteen days after this immunisation, possible delayed hypersensitivity reactions (HSR) to the antigen were sought by injecting by the intradermal route 0.025 mg of ovalbumin in the side of the animals, and 43 hours later, the reaction at the point of injection was observed. The diameter in millimiters of the reaction so-caused was measured.

Twenty one days after the injection, the animals were bled. In the serum collected, the contents of specific anti-bodies of the ovalbumin was measured by precipitation of the antibody-antigen complex in the equivalent zone. The amount of protein nitrogen contained in this precipitate was devaluated by the Folin method. The mean values of the contents of antibodies are indicated in the Table of results by the logarithm to base 2. These values express the amount, in micrograms of nitrogen precipitatable by the antigen, per millimiter of serum.

The results of these tests are as follows.

| Products tested | $\phi$mm induration after 48 h | antibodies $Log_2$ $\mu$g/ml |
|---|---|---|
| FIA controls | 0 | 9.03 ± 0.68 |
| MDP (100 $\mu$g) | 11.5 ± 2.5 | 12.31 ± 1.01 |
| MDP-(N—methyl-Ala) (100 $\mu$g) | 14 ± 0.8 | 12.51 ± 0.88 |
| MDP-(N—methyl-Ala)—$OCH_3$** | 5 ± 2 | 10.11 ± 0.6 |

**methyl ester of N—acetyl-muramyl-N—methyl-L-alanyl-D-iso-glutamine

As previously, the results obtained with the products according to the invention show the presence of a notable adjuvant effect. In addition, as will be seen below, the comparison is to the advantage of the products according to the invention when one compares the therapeutic indices, notably that corresponding to the ratio of activity/pyrogenic effect.

(2) Study Of The Toxicity And Of The Pyrogenic Effect

The toxicity of the products by parenteral administration in adrenalectomised mice, that is to say under conditions in which they are particularly sensitive to endotoxins, was studied.

It was observed that the products according to the invention, at doses at which they manifest their properties, are not toxic.

In addition, the eventuality of a pyrogenic effect in the rabbit was sought, by following the protocol of the European Pharmacopoea, Vol. 2, 1971, pages 58–60. The tests carried out notably with N-acetyl-muramyl-N-methyl-L-alanyl-D-isoglutamine or the methyl ester of the same product show the absence of a pyrogenic character. In particular, even at doses as high as 10 mg/kg of animal of N-acetyl-muramyl-N-methyl-L-alanyl-D-isoglutamine, the test remained negative; no hyperthermia was observed in the treated rabbit.

Consequently, the therapeutic index adjuvant dose/pyrogenic dose of the products according to the invention is of an order of magnitude very much higher than that of previously known adjuvant products of this type. The products according to the invention are hence particularly advantageous.

We claim:

1. A compound which is selected from the group consisting of N-acetyl-muramyl-L-(N-methyl)-alanyl-D-isoglutamine, the methyl ester of N-acetyl-muramyl-L-(N-methyl)-alanyl-D-isoglutamine and N-acetyl-Nor-muramyl-L-(N-methyl)-alanyl-D-isoglutamine.

2. The compound of claim 1, N-acetyl-muramyl-L-(N-methyl)-alanyl-D-isoglutamine.

3. The compound of claim 1, which is the methyl ester of N-acetyl-muramyl-L-(N-methyl)-alanyl-D-isoglutamine.

4. The compound of claim 1, N-acetyl-Nor-muramyl-L-(N-methyl)-alanyl-D-isoglutamine.

5. A therapeutic composition of high and improved therapeutic index which composition is virtually apyrogenic while concurrently being an effective immunostimulant, which composition comprises a biologically acceptable carrier and in a biologically effective amount, a compound selected from the group consisting of N-acetyl-muramyl-L-(N-methyl)-alanyl-D-isoglutamine, the methyl ester of N-acetyl-muramyl-L-(N-methyl)-alanyl-D-isoglutamine and N-acetyl-Nor-muramyl-L-(N-methyl)-alanyl-D-isoglutamine.

6. The composition of claim 5 wherein the compound is N-acetyl-muramyl-L-(N-methyl)-alanyl-D-isoglutamine.

7. The composition of claim 5 wherein the compound is the methyl ester of N-acetyl-muramyl-L-(N-methyl)-alanyl-D-isoglutamine.

8. The composition of claim 5 wherein the compound is N-acetyl-Nor-muramyl-L-(N-methyl)-alanyl-D-isoglutamine.

9. The composition of claim 5 which is liposome.

10. The compound of claim 5 wherein the carrier is aqueous.

11. The compound of claim 5 wherein the composition is adapted for oral, parenteral intradermal administration.

12. A therapeutic method which comprises administering to a host and stimulating the host's immunological response virtually without increasing the temperature of the host's body, a biological active composition of high and improved therapeutic index, which composition is virtually apyrogenic and effective to stimulate the host's immunological response and which composition is administered in an immunostimulating amount and comprises a biologically acceptable carrier and a compound of the formula

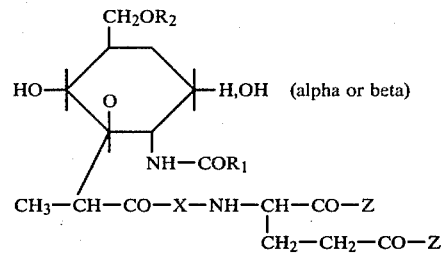

$$CH_3-CH-CO-X-NH-CH-CO-Z$$
$$\qquad\qquad\qquad\qquad\quad | $$
$$\qquad\qquad\qquad\qquad\ CH_2-CH_2-CO-Z$$

wherein Y is hydroxyl, amino or alkoxy of 1 to 10 carbon atoms, Z is hydroxyl, amino or alkoxy of 1 to 10 carbon atoms, $R_1$ is alkyl of 1 to 4 carbon atoms, $R_2$ is hydrogen or succinyl and X is N-alkyl$_{(1-4)}$-L-alanyl, N-alkyl$_{(1-4)}$-L-seryl, N-alkyl$_{(1-4)}$-L-valyl or glycyl, the second aminoacid residue being of the D-series.

13. The therapeutic method of claim 12 wherein in the compound of the composition, Y is alkoxy selected from methoxy butoxy, decanoxy, or $NHC_4H_3$.

14. The therapeutic method of claim 12 wherein in the compound of the composition, Y is alkoxy selected from methoxy butoxy, decanoxy, or $NHC_4H_3$ and X is N-alkyl$_{(1-4)}$-L-alanyl.

15. The therapeutic method of claim 12 wherein there is administered N-acetyl-muramyl-L-(N-methyl)-alanyl-D-isoglutamine.

16. The therapeutic method of claim 12 wherein there is administered the methyl ester of N-acetyl-muramyl-L-(N-methyl)-alanyl-D-isoglutamine.

17. The therapeutic method of claim 12 wherein there is administered N-acetyl-Nor-muramyl-L-(N-methyl)-alanyl-D-isoglutamine.

18. The therapeutic method of claim 12 wherein the amount administered is a dosage in the range from about 10 to 1,000 microgram per kilogram of body weight.

* * * * *